United States Patent
Rokosz et al.

(10) Patent No.: US 9,285,020 B2
(45) Date of Patent: Mar. 15, 2016

(54) OPEN BELT CLUTCH

(71) Applicants: John Rokosz, Belmont, MA (US); Philip Carvey, Bedford, MA (US); Matthew Carvey, Somerville, MA (US); Peter Costa, Medford, MA (US); Chris Holmes, Medford, MA (US)

(72) Inventors: John Rokosz, Belmont, MA (US); Philip Carvey, Bedford, MA (US); Matthew Carvey, Somerville, MA (US); Peter Costa, Medford, MA (US); Chris Holmes, Medford, MA (US)

(73) Assignee: ADICEP TECHNOLOGIES, INC, Bedford, MA (US)

( * ) Notice: Subject to any disclaimer, the term of this patent is extended or adjusted under 35 U.S.C. 154(b) by 75 days.

(21) Appl. No.: 13/781,679

(22) Filed: Feb. 28, 2013

(65) Prior Publication Data

US 2014/0238810 A1     Aug. 28, 2014

(51) Int. Cl.
*F16H 7/08* (2006.01)
*F16D 13/10* (2006.01)
*A61F 2/68* (2006.01)

(52) U.S. Cl.
CPC .............. *F16H 7/0827* (2013.01); *F16D 13/10* (2013.01); *A61F 2002/6845* (2013.01)

(58) Field of Classification Search
CPC .............................................. A61F 2002/6845
USPC .......................................... 192/72, 73, 79, 80
See application file for complete search history.

(56) References Cited

U.S. PATENT DOCUMENTS

| | | | | |
|---|---|---|---|---|
| 508,663 A * | 11/1893 | Wakefield et al. | | 192/80 |
| 701,489 A | 6/1902 | Love | | |
| 759,764 A | 5/1904 | Snyder | | |
| 759,841 A * | 5/1904 | Davis | | 192/80 |
| 988,182 A * | 3/1911 | Ewald | | 464/40 |
| 1,034,514 A * | 8/1912 | Rufe | | 192/80 |
| 1,064,435 A * | 6/1913 | Blystone | | 192/80 |
| 1,099,636 A * | 6/1914 | Carter | | 192/80 |
| 1,153,853 A | 9/1915 | Pfeiffer | | |
| 1,170,643 A * | 2/1916 | Jones | | 192/80 |
| 1,173,849 A * | 2/1916 | Oberley et al. | | 192/80 |
| 1,176,321 A * | 3/1916 | Ruemelin | | 192/80 |
| 1,252,050 A * | 1/1918 | Stinson | | 192/80 |
| 1,439,952 A * | 12/1922 | Daniels | | 192/78 |
| 1,440,226 A * | 12/1922 | Lott | | 192/80 |
| 1,456,126 A | 5/1923 | Friday | | |
| 1,529,828 A | 3/1925 | Barlow | | |
| 1,594,259 A | 7/1926 | Hardman | | |
| 2,335,848 A | 12/1943 | Dodwell | | |
| 2,479,965 A | 8/1949 | Ragsdale | | |
| 2,518,453 A | 8/1950 | Dodwell | | |
| 2,566,539 A | 9/1951 | Starkey | | |
| 2,576,605 A | 11/1951 | Hupp | | |
| 2,734,606 A | 2/1956 | Bellamy | | |
| 2,774,455 A | 12/1956 | Goldberg | | |
| 3,171,523 A | 3/1965 | Shoquist et al. | | |
| 3,193,254 A | 7/1965 | Minnick | | |

(Continued)

*Primary Examiner* — Rodney H Bonck
(74) *Attorney, Agent, or Firm* — The Patent Practice of Szmanda & Shelnut, LLC; Charles R. Szmanda; James G. Shelnut

(57) ABSTRACT

The present application for patent provides a belt clutch having a drum with a drum-side friction surface, an open ended belt with a belt-side friction surface, and an externally controlled actuator on one end of the belt. The belt is configured to be coupled to a source of torque on the other end of the belt. The belt-side and drum-side friction surfaces engage frictionally when in use, such that the effective coefficient of friction between the drum-side friction surface and the belt-side friction surface varies across the width or length of the belt.

19 Claims, 8 Drawing Sheets

(56) References Cited

U.S. PATENT DOCUMENTS

| | | | |
|---|---|---|---|
| 3,483,955 A | 12/1969 | Schell et al. | |
| 3,583,531 A * | 6/1971 | Besoyan | 188/77 R |
| 3,828,895 A * | 8/1974 | Boaz | 188/77 R |
| 3,962,936 A | 6/1976 | Lewis | |
| 4,031,768 A * | 6/1977 | Henderson et al. | 474/250 |
| 4,102,441 A | 7/1978 | Kohlhage | |
| 4,290,512 A | 9/1981 | Zindler | |
| 4,598,807 A | 7/1986 | Clegg | |
| 4,602,706 A * | 7/1986 | Blinks et al. | 188/259 |
| 4,795,013 A | 1/1989 | Latsko | |
| 4,987,804 A | 1/1991 | Greenawalt | |
| 5,012,905 A | 5/1991 | Tanaka | |
| 5,102,411 A | 4/1992 | Hotchkiss et al. | |
| 5,197,928 A * | 3/1993 | Mishima et al. | 474/263 |
| 5,401,011 A | 3/1995 | Gatenby et al. | |
| 6,044,943 A * | 4/2000 | Bytzek et al. | 192/41 R |
| 6,260,671 B1 | 7/2001 | Fujita | |
| 6,622,833 B2 | 9/2003 | Baumann et al. | |
| 6,902,048 B1 | 6/2005 | Chung | |
| 6,948,400 B2 | 9/2005 | Nakamura et al. | |
| 7,219,774 B2 | 5/2007 | Fujii et al. | |
| 7,410,472 B2 | 8/2008 | Yakimovich et al. | |
| 986,923 A1 | 3/2011 | Knapp | |
| 7,947,004 B2 | 5/2011 | Kazerooni et al. | |
| 7,985,193 B2 | 7/2011 | Thorsteinsson et al. | |
| 8,052,629 B2 | 11/2011 | Smith et al. | |
| 2004/0154883 A1 | 8/2004 | Fujii et al. | |
| 2006/0096813 A1 | 5/2006 | Fujita | |
| 2006/0211966 A1 | 9/2006 | Hatton et al. | |
| 2007/0032884 A1 | 2/2007 | Veatch | |
| 2009/0192619 A1 | 7/2009 | Martin et al. | |
| 2011/0127131 A1 * | 6/2011 | Simons et al. | 188/77 R |
| 2012/0016493 A1 | 1/2012 | Hansen et al. | |

* cited by examiner

OPEN BELT CLUTCH

STATEMENT OF GOVERNMENT SUPPORT

The subject matter of the present application was made with Government support from the National Science Foundation under contract number IIP-1152605. The Government may have rights to the subject matter of the present application.

FIELD OF THE INVENTION

The present application for patent is in the field of frictional clutches and in particular, clutches in which friction is applied by an open ended belt so that controllably engaging the clutch through a partial turn and/or a small number of turns may be accomplished.

BACKGROUND

In general, a clutch is a mechanism for alternately establishing and disestablishing a coupling relationship, wherein, when actuated, an input for supplying mechanical energy is coupled to an output wherein mechanical energy is delivered. Clutches are known in a variety of designs for a variety of applications. Among these are various kinds of friction clutches such as multiple plate clutches, centrifugal clutches, cone clutches, or basket clutches, non-slip clutches such as "dog" clutches, hydraulic clutches that employ a viscous fluid as a coupling medium, electromagnetic clutches, wrap spring clutches and belt clutches.

Various belt-type clutches are known. For example, the patent to Hupp, U.S. Pat. No. 2,576,605, discloses and claims a combination, including a "V-belt disposed to clutch a drive sheave for power transmission and wherein the belt is loose on the sheave when declutched therefrom, a pair of guides for the belt to control the clutching action of the belt when the belt is tightened upon the sheave, each guide being disposed to engage the outer surface of a flight of the belt adjacent the sheave, and a single support for said guides disposed to provide freedom of floating action therefor under the influence of said belt and to maintain said guides in spaced relation correlated to the spacing of the belt flights in final clutch tightened position to effect a tensioning of the belt." However, the clutch described in Hupp is designed for power transmission. The clutch has a continuous V-belt, arranged to transfer power between a driven rotating shaft and a rotatable shaft and is not suitable for controllably engaging through a fractional turn and/or a small number of turns, As a further example, the patent to Love, U.S. Pat. No. 701,489 discloses and claims a belt wrench, having "a handle portion, the forward end of said handle portion being curved upward to form the contact point or nose . . . , an opening formed through the handle portion at the forward part thereof, a strip of flexible material secured to the underside of the handle portion at a point in the rear of the opening, a bolt passing upward through the flexible strip and through the handle portion and having a nut threaded upon its upper end for the purpose of securing the strip to the handle, said strip passing from its point of securement upward through the opening around the object to be gripped and back again through the opening . . . " However, while belt wrenches can perform a frictional gripping function via the belt, the frictional grip is not varied under the control of an actuator to give a controllable frictional grip.

Despite the evident capabilities of conventional belt clutches and belt gripping tools such as belt wrenches, there remains a need for a clutching device that is capable of controllably engaging through angles ranging from a fractional turn through a small number of turns.

DETAILED DESCRIPTION OF THE DRAWINGS

FIG. 1(a) illustrates a schematic free body diagram of a capstan effect clutch. A drum 101 is wrapped either partially or fully by a belt 102. The figure further illustrates a "hold" tension, $T_{hold}$ 103, a "load" tension, $T_{load}$ 104, applied to the drum through a wrap angle, $\theta$, 105, usually expressed in radians. FIG. 1(b) illustrates a free body force diagram of a V-belt 106, generally mated to another frictional surface on the drum (not shown). The bevel on the belt has an angle of $\beta$ 107. The size of the frictional force on the sidewall 108, is determined by the bevel angle, $\beta$, the radial force between the belt and the and the drum, $F_1$, and the coefficient of friction, $\mu$, characteristic of the engaging surfaces.

Figure 2:
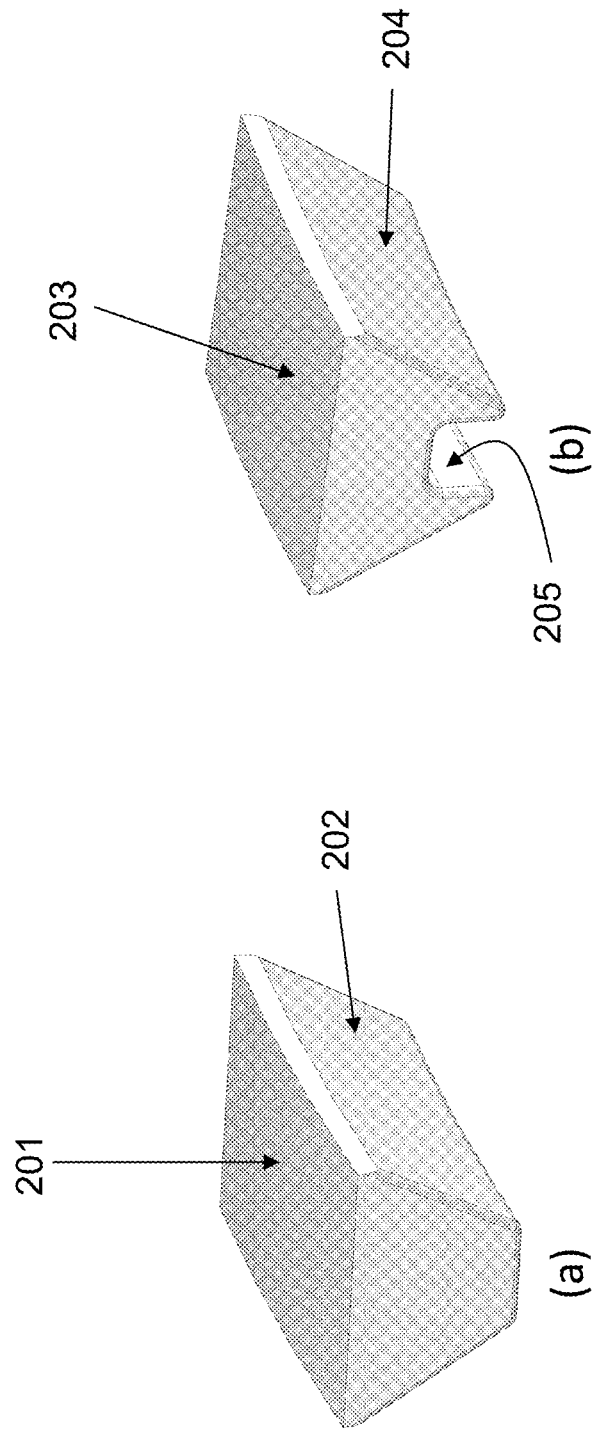
FIG. 2(a) illustrates a segment of a belt of generally polygonal cross section.
FIG. 2(b) illustrates a segment of a belt of generally polygonal cross section having a groove along the length of the belt.

FIG. 2(a) illustrates a segment of a belt having a base surface, 201, and a frictional surface, 202. FIG. 2(b) illustrates a segment of a belt having a base surface, 203, a frictional surface, 204, and a groove along the length of the belt, 205, wherein the groove is configured to retain a spring for holding the belt-side friction surface, 204, generally out of contact with the drum-side friction surface.

FIG. 3(a) illustrates an exploded view of an embodiment of a belt, having a base, 301, to which may be attached friction materials 305 and 306. The friction materials may be flat, 305 or of other generally polygonal cross section, 306 and have two or more portions with different frictional characteristics, represented by the different shadings of 305 and 306. FIG. 3(a) also illustrates an end to be anchored, 302, slots 303 and 304, which configure the belt to be wrapped multiple times around the drum and a free end, 307, to be attached to an actuator. FIG. 3(b) illustrates an embodiment of a portion of a clutch, wherein the belt is configured to be wrapped twice around the drum, 308, by threading the free end, 307 through the slots 303 and 304 to form areas of engagement in which the belt-side friction surface engages frictionally with the drum-side friction surface.

Figure 3:
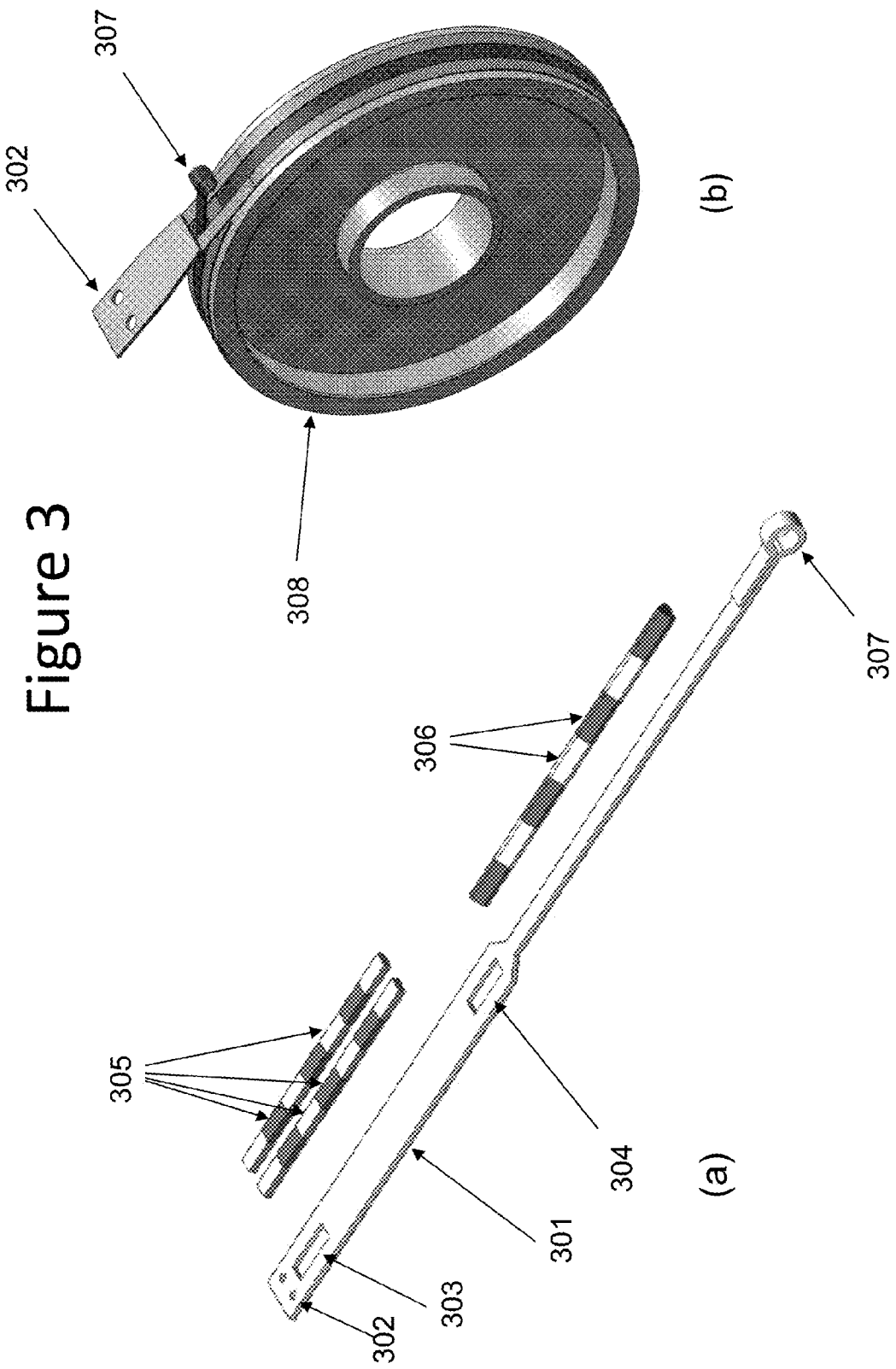
FIG. 3(a) illustrates an exploded view of an embodiment of a belt.
FIG. 3(b) illustrates a portion of a clutch with the belt of FIG. 3(a) wrapped twice around a drum.
Figure 4:
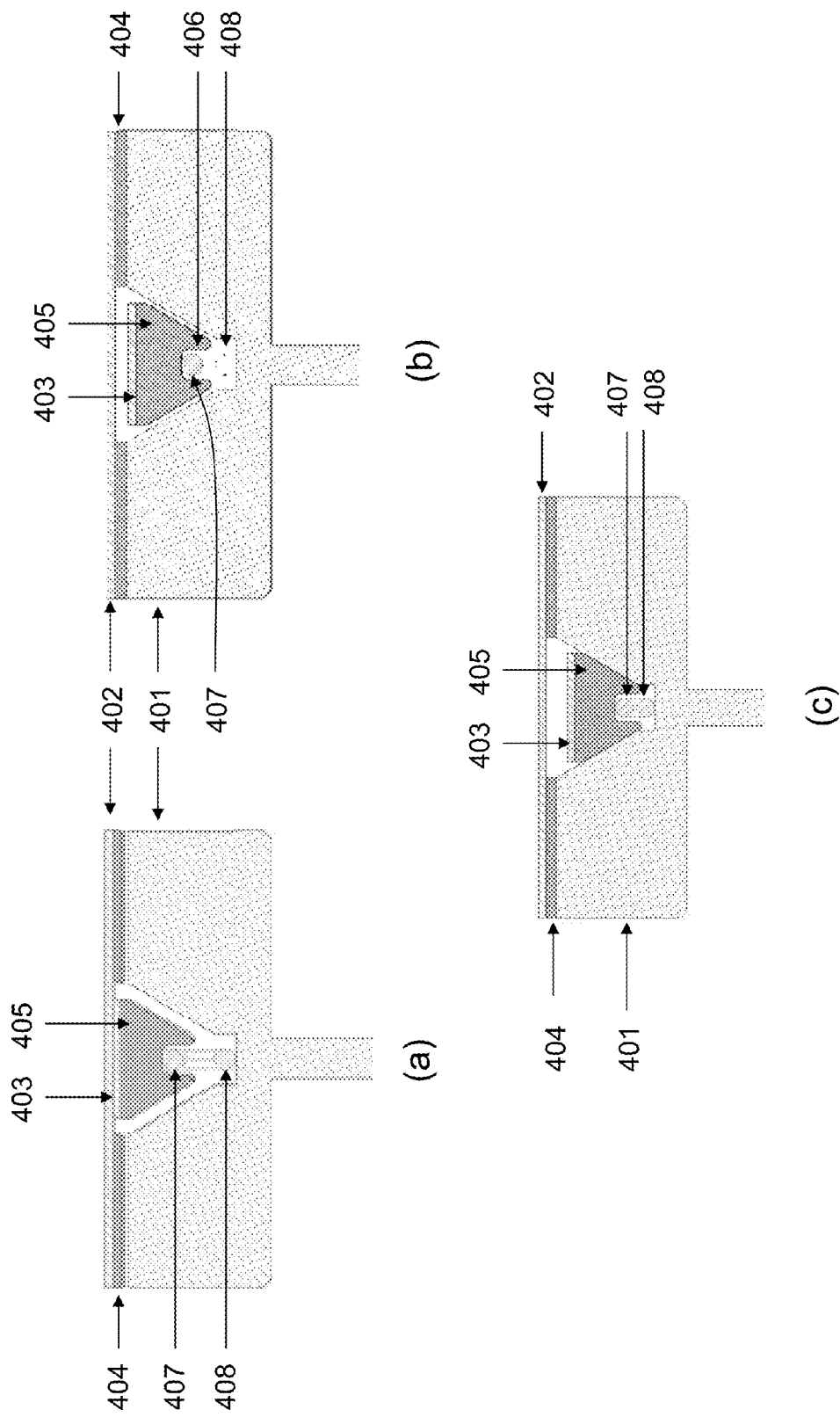
FIG. 4 illustrates a cross section of the frictional engagement areas of the clutch portion as assembled in FIG. 3(b), at various levels of engagement.

FIG. 4 illustrates a cross section of the frictional engagement areas of the clutch portion as assembled in FIG. 3(b). The drum body, 401, is double wrapped by the belt, which comprises a wide portion of the base, 402, a narrow portion of the base, 403, strips of flat friction material, 404, and a piece of friction material of generally polygonal cross section, 405, but with a groove along the length of the belt, 406, wherein the groove is configured to retain a spring for holding the belt-side friction surface generally out of contact with the drum-side friction surface in absence of sufficient supplied force to the free end of the belt. Further shown in schematic cross section is a wavy spring in which the crest of the wave, 407, is sampled in the plane of the cross section and the trough of the wave, 408 is sampled either circumferentially in front of or circumferentially behind the cross section. FIG. 4(a) shows the clutch fully disengaged with the flat friction strips, 404, and the friction material of generally polygonal cross section, 405, held out of contact by the wavy spring. As the hold tension on the belt is increased, the forces exerted by the wavy spring are overcome. FIG. 4(b) shows the clutch partially engaged with the flat friction strips, 404, engaging the drum-side friction surface and the friction material of generally polygonal cross section, 405, still held out of contact by the wavy spring. FIG. 4(c) shows the clutch fully engaged with the flat friction strips, 404, and the friction material of generally polygonal cross section, 405, held in contact with their respective drum-side friction surfaces.

Figure 5:
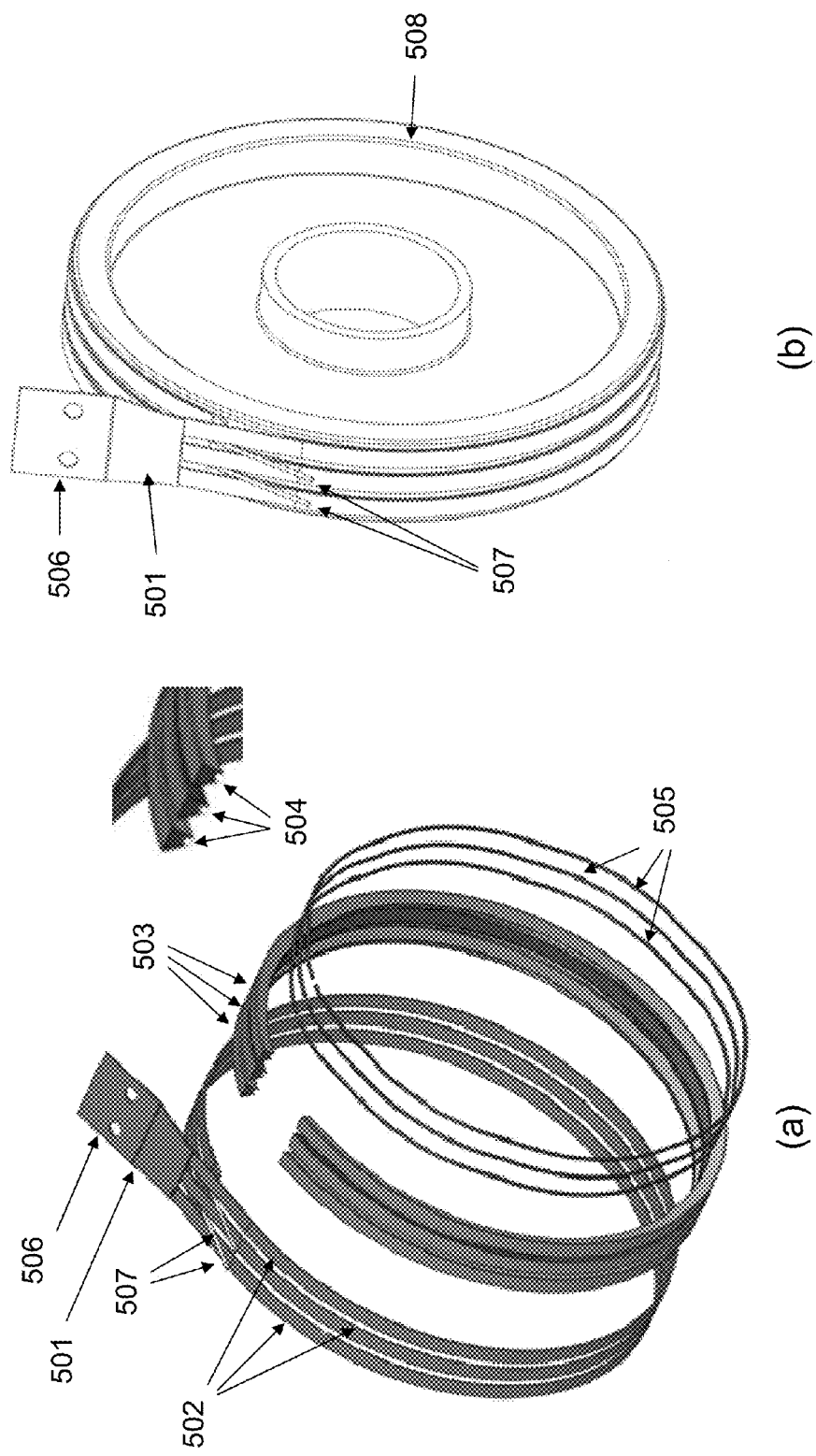
FIG. 5(a) illustrates an exploded view of another embodiment of a belt, having a spring.
FIG. 5(b) illustrates a portion of an assembled clutch with the belt of FIG. 5(a).

FIG. 5(a) illustrates an exploded view of another embodiment of a belt, comprising a base, 501, divided into three parallel portions, 502, such that the effective coefficient of friction between the belt-side friction surface and the drum-side friction surface varies across the total width of the belt. The pieces of friction material that present one or more belt-side friction surfaces, 503, are attached to their respective base portions and are of generally polygonal cross section. The friction materials, 503 have grooves along their respective lengths, 504, configured to retain a spring for holding the belt-side friction surface generally out of contact with the drum-side friction surface in absence of sufficient supplied force to the free end of the belt. The springs, 505, shown as wavy springs in this embodiment, are fitted in the grooves when the belt is assembled. The belt is configured to be anchored at 506, on a frame and accommodating an actuator that applies a force at the free end, 507. FIG. 5(b) illustrates an embodiment of a portion of a clutch, wherein the belt is configured to be tension wrapped around the outside of the drum, 508, by threading the free end, 507 through the slots formed by the three parallel portions, 502.

FIG. 6(a) illustrates an open ended belt having a base, 601, an end to be anchored, 602, a free end to be coupled to an actuator, 603, and multiple segmented protrusions attached to the base, 604, said protrusions comprising friction material and having a generally polygonal cross section. FIG. 6(b) illustrates a cutaway view of a portion of a clutch having a compression wrap on the inside of the drum, 605. The drum-side friction surface, 606, has a cross section of generally polygonal shape having 4 sides in this embodiment. Moreover, the drum-side friction surface is on the inside of the drum, such that the belt is wrapped as a compression wrap. The belt is configured to be anchored at 602, on a frame separate from the drum and a movable free end, 603, to be controlled by the actuator, and multiple segmented protrusions attached to the base, 604, said protrusions comprising friction material and having a generally polygonal cross section.

Figure 7:
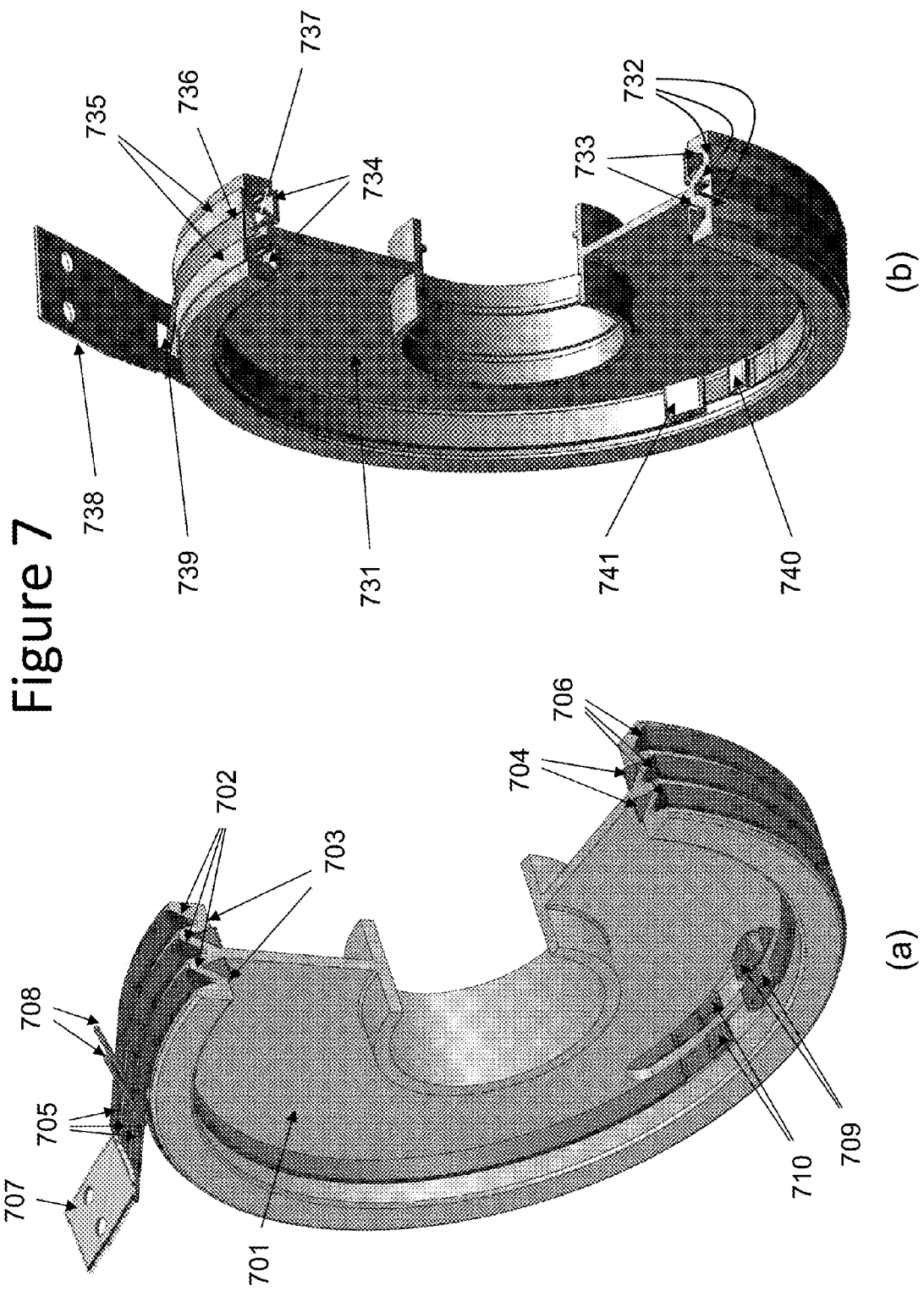
FIG. 7(a) illustrates a cutaway view of an embodiment of a portion of a clutch, wherein the belts are both compression and tension wrapped.
FIG. 7(b) illustrates a cutaway view of yet another an embodiment of a portion of a clutch, wherein the belts are both compression and tension wrapped.

FIG. 7(a) illustrates a cutaway view of a portion of a clutch, wherein the belts are both compression and tension wrapped. The drum, 701, has three outer engagement regions, 702, and two inner engagement regions, 703. Two belts, 704, are compression wrapped on the inside of the drum. The tension-wrapped belt on the outside of the drum comprises three parallel portions, each comprising a base portion, 705, and friction material of generally polygonal cross section, 706. The cross sections of the inner compression wrapped belts, 704 and the inner engagement regions of the drum, 703, are configured generally to mate with each other. The cross section of the outer tension wrapped belt, 706 and the outer engagement regions of the drum, 702, are configured generally to mate with each other. The outer tension wrapped belt has an anchored end, 707, and a free end, 708, which is coupled to an actuator (not shown). The inner compression wrapped belts each have an anchored end (b which can be attached together through the cutout), 709, and a free end (which can be attached together through the cutout), 710, which is coupled to an actuator (not shown).

FIG. 7(b) illustrates a cutaway view of a portion of a clutch, wherein the belts are both compression and tension wrapped. The drum, 731, has three outer engagement regions, 732 similar to those found in FIG. 3(b), and two inner engagement regions, 733. Two belts, 734, are compression wrapped on the inside of the drum. The tension-wrapped outer belt comprises three parallel portions, two flat but of generally polygonal cross section, 739, and one having a friction material of generally polygonal cross section, 736, 737. The cross sections of the inner compression wrapped belts, 734, and the inner engagement regions of the drum, 733, are configured generally to mate with each other. The cross section of the outer tension wrapped belt, 735-737, and the outer engagement regions of the drum, 732, are configured generally to mate with each other. The outer tension wrapped belt has an anchored end, 738, and a free end, 739, which is coupled to an actuator (not shown). The inner compression wrapped belts each have an anchored end (one of which is shown), 741, and a free end (one of which is shown), 740, which is coupled to an actuator (not shown).

Figure 8:
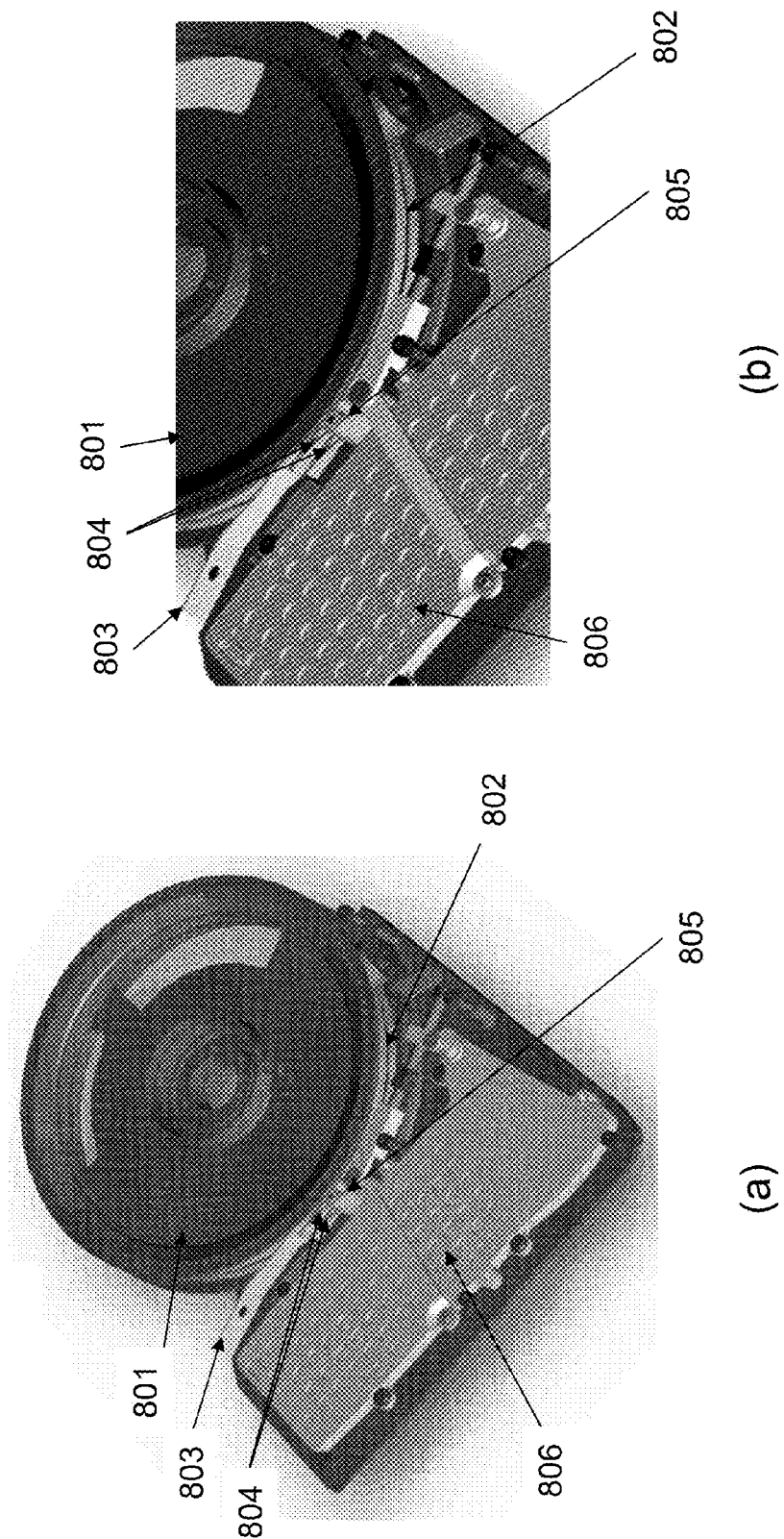
FIG. 8 illustrates an assembled clutch in full and close-up views.

FIG. 8(a) illustrates an assembled clutch. Shown in the figure are the drum, 801, an outer belt, 802, having an anchored end, 803, and a free end, 804, attached to an actuator, 805. The actuator is controlled by a control module, 806. FIG. 8(b) illustrates a close-up drawing of the assembled clutch, showing the drum, 801, the outer belt, 802, having an anchored end, 803, and a free end, 804, attached to an actuator, 805 which is controlled by a control module, 806.

DETAILED DESCRIPTION

As used herein, the conjunction "and" is intended to be inclusive and the conjunction "or" is not intended to be exclusive unless otherwise indicated. For example, the phrase "or, alternatively" is intended to be exclusive.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting.

As used herein, the terms "having", "containing", "including", "comprising," "with," and the like are open ended terms that indicate the presence of stated elements or features, but do not preclude additional elements or features. The articles "a", "an" and "the" are intended to include the plural as well as the singular, unless the context clearly indicates otherwise. As used herein, references to "first" may include "first and only." As used herein, "a protrusion" or "protrusions" are understood as projecting so as to make frictional contact.

As used herein, it is understood that a belt configured to form a wrap partially, fully or a plurality of times around the drum may be further configured to form a tension wrap on the outside drum surface or a compression wrap on the inside drum surface. And as used herein, it is understood that a drum-side surface includes both the inside and outside drum surfaces.

As used herein, variations in the effective coefficient of friction can occur as the result of variations of the geometry of frictional engagement or because of variations in the friction materials used for frictional engagement.

Selected cross sections may include cross sections found in a newly made drum or belt as well as cross sections in drums or belts that have undergone mechanical wear due to abrasion.

Disclosed and claimed herein is a clutch having: a drum with an axis, a radius, a drum-side friction surface, and a selected cross section bounded by the drum-side friction surface; an open-ended belt, with an anchored end, a free end, a length, a width, a belt-side friction surface, and a selected cross section bounded by the belt-side friction surface, configured to form a wrap partially, fully or a plurality of times around the drum; and an externally controllable actuator, configured to apply a force to the free end of the open ended belt, whereby the belt-side friction surface engages frictionally with the drum-side friction surface, wherein the cross section of the drum and the cross section of the belt are configured generally to mate with each other, and wherein the effective coefficient of friction between the belt-side friction surface and the drum-side friction surface varies across the width or length of the belt.

Further disclosed and claimed herein is a clutch having a drum with a radius, m outer engagement regions, and n inner engagement regions, wherein each of the m outer engagement regions and each of the n inner engagement regions has a selected cross section bounded by a drum-side friction surface, and wherein m and n may be the same or different and m=0 to 6, and n=0 to 6, subject to the condition that m+n=1 to 12, p open ended-belts, each open ended belt configured to form a wrap partially, fully or a plurality of times around its corresponding outer engagement region or its corresponding inner engagement region, wherein each of the p open ended belts has an anchored end, a free end, a length, and a selected cross section bounded by a belt-side friction surface, and wherein the selected cross section of each of the one or more open ended belts is configured generally to mate with the selected cross section of its corresponding inner or outer engagement region, and wherein p=1 to m+n; means for applying a force to each open-ended belt, whereby said each open ended belt is engaged frictionally with its corresponding inner or outer engagement region.

A further embodiment may include a clutch having a means for holding the first or second belt-side frictional surfaces generally out of contact with the first or second drum-side frictional surfaces, respectively. This may be accomplished using an expansion spring such as a wavy spring or other stiff material in the construction of the belt. The expansion spring may be embedded or otherwise incorporated into the belt by installing it into a channel, slot, groove or conduit in the protrusion as is shown in FIG. 5(a). Such materials may be in the form of music wire, such as piano wire, available from the Grainger Company of Lake Forest Ill. Further, the expansion ring may be incorporated into the backing by using, for example, a stiff planar material, comprising, spring steel, or other stiff metals available from, for example, the Mechanical Metals Company of Newtown, Pa.

Further means for holding the first or second belt-side frictional surfaces generally out of contact with the first or second drum-side frictional surfaces, respectively may comprise combinations of springs and pistons. Further means for holding the first or second belt-side frictional surfaces generally out of contact with the first or second drum-side frictional surfaces, respectively may comprise a wavy spring or other equivalent structure. Wavy springs and other types of expansion springs may be obtained from the Smalley Steel Ring Company of Lake Zurich, Ill.

Figure 6:
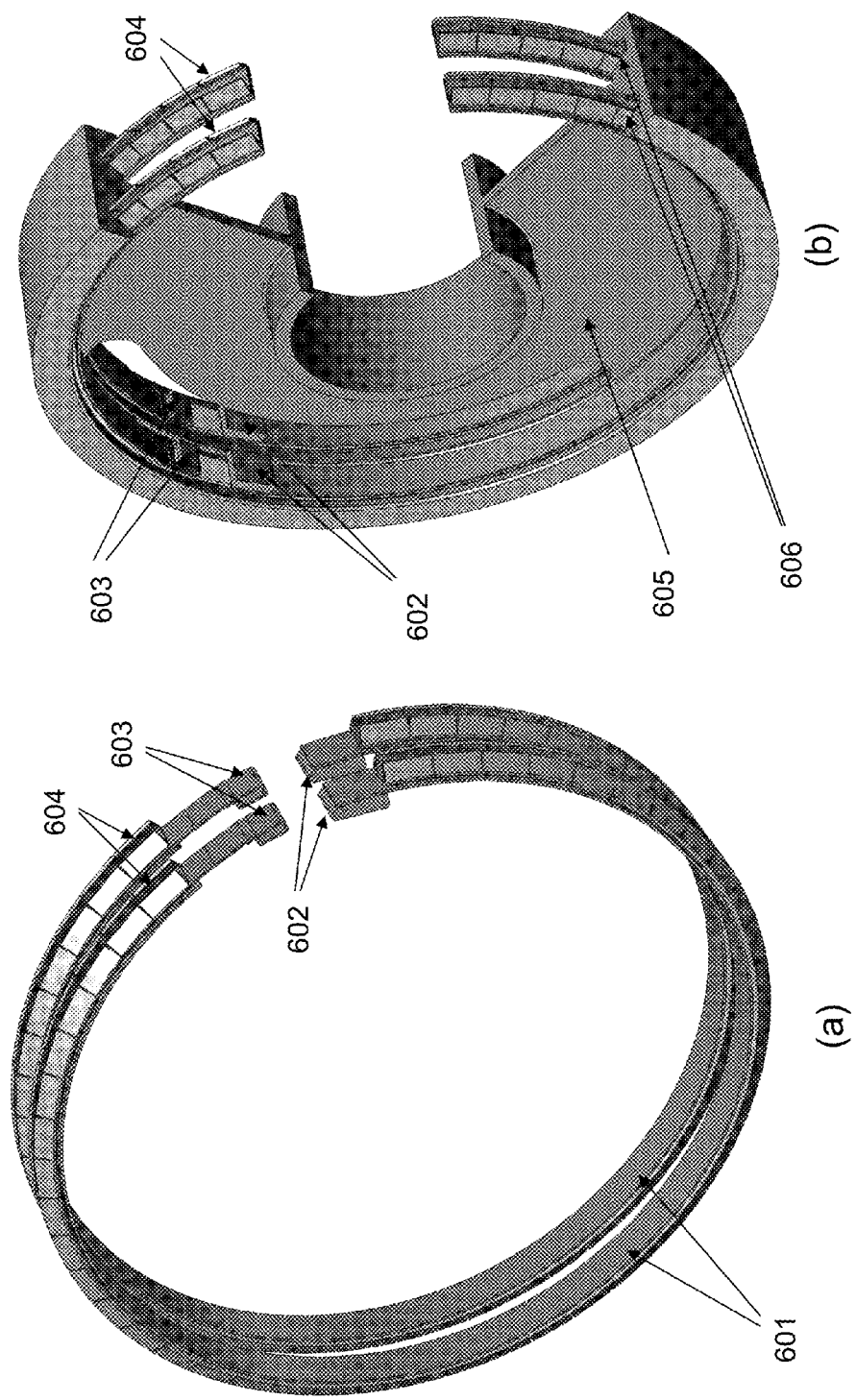
FIG. 6(a) illustrates an open ended belt having multiple segmented protrusions of generally polygonal cross section.
FIG. 6(b) illustrates how the belt of FIG. 6(a) is compression wrapped around the inside of drum.

The belt-side friction surface may include a flat band, engineered to present a selected coefficient of friction with its corresponding drum-side surface. In addition, the belt may present a shaped frictional surface comprising a curved or polygonal shape such as a triangle, a quadrilateral or other polygon having 2-20 sides. Moreover, it is understood that the polygon may have a general polygonal shape but have other features such as grooves or conduits without departing from the spirit of the invention. The shaped protrusion may mate with a corresponding feature on the drum by itself or be a part of a larger cross section comprising the shaped protrusion and a flat band. Shaped materials may be of unitary construction or comprise arc segments as shown in FIG. 3 and FIG. 6. Moreover, the shaped protrusions may be attached to a base structure such that the base extends laterally beyond the contacting surface of the shaped protrusion (see FIG. 3) or is flush with the contacting surface of the shaped protrusion. In addition to polygonal cross sections, the belt-side friction surface may be curved with a cross section of semicircular, ovular or other curved cross section.

The shaped protrusion, comprising friction material or other material having a frictional surface may be attached to a base using one or more staples, screws, rivets, grommets, glue, material fusion, welds, solder, brazing or equivalents thereof. Moreover, the shaped protrusion and the base may together be of unitary construction. Still further, the shaped protrusion may be attached to the base by keying, the shaped protrusion to the belt, using, for example, slotting, dove tailing or the equivalent. Still further, the base may be embedded within the shaped protrusion. It may prove useful to segment the shaped protrusions or any other portions of the belt by introducing grooves, notwithstanding the fabrication type.

Frictional surfaces may be manufactured in various ways. For example, the drum may present a sandblasted and hardened friction surface comprising aluminum, titanium, steel, or other metal or ceramic material. Both the inside surface of the stainless steel portion of the band and the friction surface on the drum are both hardened using an arc spray process or equivalent process to give a hardness of Rockwell C55-C65 or equivalent. Metal frictional surfaces may be made by sandblasting, chemical etching, sanding using hard abrasives such as garnet zircon, alumina or diamond, plasma or reactive ion etching, ion milling, equivalents thereof or combinations thereof. Roughened surfaces may also be made by coatings comprising a binder and an abrasive material such as calcite, emery, purified corundum, diamond, novaculite, pumice, rouge, silica, borazon (cubic boron nitride), ceramic composites, ceramic aluminum oxide, ceramic iron oxide, steel abrasive, silicon carbide, zircon, alumina-silica, alumina, garnet, zinc oxide, carbon fiber, graphene, equivalents thereof or mixtures thereof. Abrasive materials in the coatings may include powders, fibers sheets or engineered shapes and their dimensions may range in size from 1 nm (nanometer) to 500 µm (micrometers). Roughness may be of a selected pattern or random.

Belts may be of various designs such as Kevlar banded belts, banded cogged v-belts, serpentine belts, variable speed v-belts, Kevlar v-belts, poly chain GT carbon belts or equivalents thereof. Such belt designs are available commercially from V-Belt Global Supply, LLC.

Belts may incorporate other materials in addition to roughened metal or the belt may be of unitary construction without an attached band. Belt materials may further include leather, cloth webbing, or a filled or unfilled polymer material, also known as "friction materials"; wherein the polymer material may be balata or other rubber, polyethylene, polypropylene, novolak, resol, fluoropolymers such as poly-tetrafluoroethylene, polyvinyl chloride, equivalents thereof or combinations thereof. It may be desirable to use polymer materials having a limited elasticity such as balata to avoid belt creep. Belts may take on different shapes and different combinations of shapes. For example a flat belt with a triangular of quadrilateral protrusion may be used; wherein both the flat portion and the protrusion present a frictional surface to the frictional surface of the drum. Moreover, belts can be engineered so that clutched with selected mechanical advantages can be made. This may include modifying the planar coefficient of friction or it may include modifying the effective coefficient of friction by using a belt with a selected angle. While most commercially available V-belts have a 40° angle between the faces ($\beta=0°$), except for V series (aka "Harvester" or "Wedge" belts), which have a 30° angle between the faces ($\beta=15°$), belts with specifically tailored angles may also be used.

As noted above, polymer materials may be filled with various abrasives, including but not limited to, calcite, emery, purified corundum, diamond, novaculite, pumice, rouge, silica, borazon (cubic boron nitride), ceramic composites, ceramic aluminum oxide, ceramic iron oxide, steel abrasive, silicon carbide, zircon, alumina-silica, alumina, garnet, zinc oxide, carbon fiber, graphene, equivalents thereof or mixtures thereof. Fillers may include powders, fibers sheets or engineered shapes and their dimensions may range in size from 1 nm (nanometer) to 500 µm (micrometers). Friction materials are commercially available from Ferotec Friction, Inc. of Mount Joy, Pa.

Frictional surfaces may also be imparted to belts by abrasive blasting, bead blasting, chemical etching, sanding using hard abrasives such as garnet zircon, alumina or diamond, plasma or reactive ion etching, ion milling, equivalents thereof or combinations thereof. Roughened surfaces may also be made by coatings comprising a binder and an abrasive material such as calcite, emery, purified corundum, diamond, novaculite, pumice, rouge, silica, borazon (cubic boron nitride), ceramic composites, ceramic aluminum oxide, ceramic iron oxide, steel abrasive, silicon carbide, zircon, alumina-silica, alumina, garnet, zinc oxide, carbon fiber, graphene, equivalents thereof or mixtures thereof. Abrasive materials in the coatings may include powders, fibers sheets or engineered shapes and their dimensions may range in size from 1 nm (nanometer) to 500 µm (micrometers). Roughness may be of a selected pattern or random.

In addition to having single protrusions, a belt may have one or more protrusions in parallel to each other. Examples are shown in FIG. 3 and FIG. 6. Such features in the belt, generally mated to corresponding features corresponding features in the drum allow load sharing on the abrading components; thus reducing mechanical wear.

It should be further noted that selected cross sections may include cross sections found in a newly made drum or belt as well as cross sections in drums or belts that have undergone mechanical wear due to abrasion. Clutches showing wear in either the drum or the belt do not depart from the scope of the invention. Accordingly, it is contemplated, for example, that polyhedral shapes may have rounded corners as the features of the drum and belt undergo wear.

Segmented protrusions in the belt may be configured so that they are spaced between about 100 µm (micrometers) to about 5 mm apart or they may be spaced regularly at larger distances. Smaller spacings usually do not require a corresponding feature at the drum side frictional surface. However, for larger spacings a corresponding feature may be incorporated as a part of the drum-side frictional surface. This arrangement provides timing functionality as well as more precision in angular control.

Also contemplated in this disclosure are multilevel clutches that can couple torques from multiple sources to the drum and each coupling may provide greater mechanical advantage with less wear to the frictional surfaces. An embodiment of a multilevel clutch is shown in FIG. 7(b). The drum, shown in cross section, with an outer drum-side frictional surface, a belt, also shown in cross section, with the selected cross section of the belt configured generally to mate with the selected cross section of its corresponding drum-side frictional surface. The belt is anchored at 738 to one source. Also shown are two inner drum-side frictional surfaces, situated below the outer drum-side frictional surface and shown in cross section, and two belts, also shown in cross section, with the selected cross sections of the belts configured generally to mate with the selected cross sections of their corresponding drum-side frictional surfaces. This belt, is anchored to a second source at 741. Additional levels may be advantageous. For example, clutches having 3-10 levels are also contemplated.

Means for applying a force to the free end of an open ended belt include hydraulic pistons, pneumatic pistons, electromagnetic pistons, rotating motors, linear motors, servo motors, gears, screw actuators such as a screw jack, a ball screw or a roller screw, linear actuators, comb drives, piezoelectric actuators and amplified piezoelectric actuators, thermal bimorphs, electroactive polymers, photoactive polymers, winches, equivalents thereof or combinations thereof. Actuators that provide a means for applying a force to the free end of an open ended belt may be obtained from the Warner Linear Company of Belvedere Ill., the Progressive Automations Company of Richmond BC, Canada, or Lenco Marine Inc. of Stewart Fla. Actuators may be configured to tighten the belt around the drum by applying a force to the free end of the belt or to push the belt at its non-contact side into it's mated drum-side frictional surface.

EXAMPLES

Overview

Figure 1:
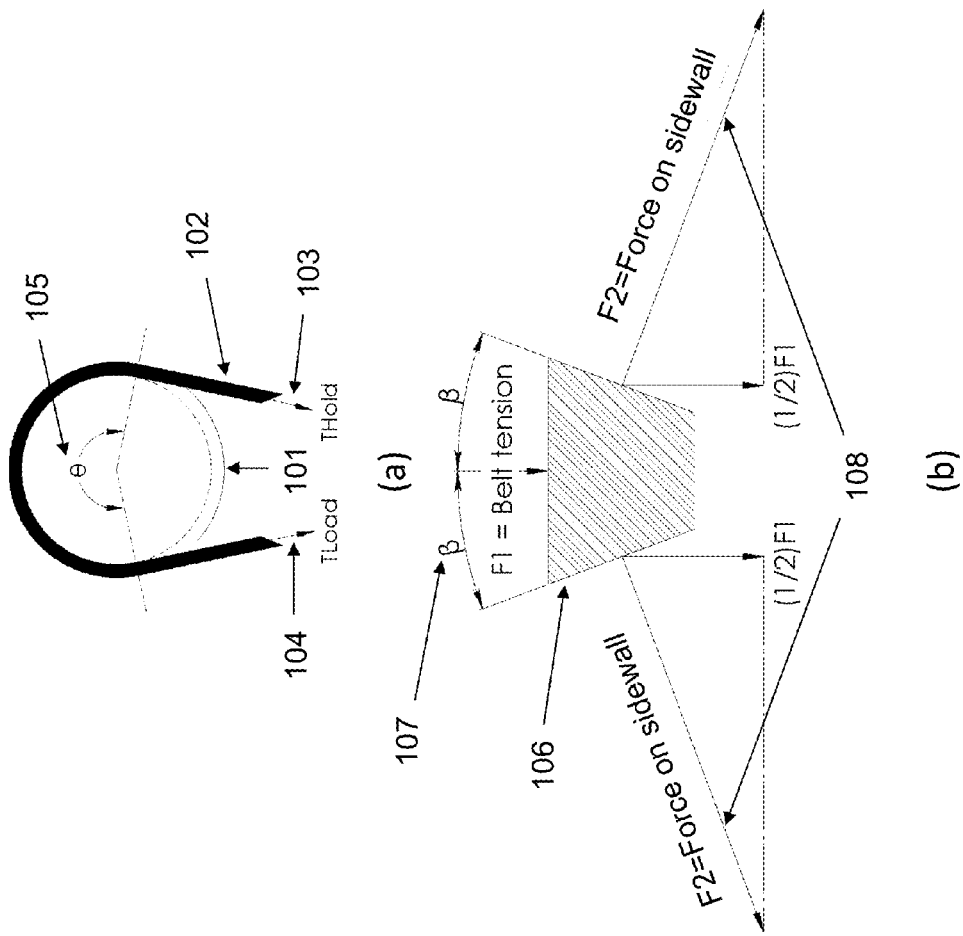
FIG. 1(a) illustrates a schematic free body diagram of a capstan effect clutch.
FIG. 1(b) illustrates a free body force diagram of a V-belt, generally mated to another frictional surface.

The diagram of the capstan in FIG. 1 and Eytelwein's formula can be used to calculate the mechanical advantage of a belt clutch. In the simplest case of a flat band on a drum, the mechanical advantage is the load force $F_{load}$ divided by the holding force $F_{hold}$ (that force just necessary to prevent slippage) is given by $$MA = \frac{F_{load}}{F_{hold}} = e^{\mu \cdot \theta} \Rightarrow \ln\left(\frac{F_{load}}{F_{hold}}\right) = \mu\theta \quad (1)$$

where μ is the coefficient of friction between the drum and the belt and θ is the wrap angle expressed in radians. For a flat belt, the force due to friction, $F_{friction}$, just at the point of slipping is given by $$F_{friction}(\text{flat}) = F_r \cdot \mu \quad (2)$$

where $F_r$ is the radial force between the flat band and the drum.

For belts of different geometry, larger frictional forces can be obtained. For example, with reference to FIG. 1(b), a V-belt, configured generally to mate with a V-groove in a drum has a frictional force given by $$F_{friction}(V \text{ belt}) = \frac{F_r \cdot \mu}{\sin(\beta)} \quad (3)$$

where β is one-half of the angle subtended by the V-belt and measured relative to the radius as shown in FIG. 1(b). The parameter, μ/sin(β), is an effective coefficient of friction for the V-belt geometry. Accordingly, the mechanical advantage obtained for a V-belt clutch is given by $$MA(V \text{ belt}) = \frac{F_{load}}{F_{hold}} = e^{\left[\frac{\mu \cdot \theta}{\sin(\beta)}\right]} \quad (4)$$

Example 1

For a flat band clutch having a coefficient of friction between the band and the drum of 0.401, and requiring a mechanical advantage of 125, equation (1) is used to compute the required wrap angle, θ, to be 12.04 radians of arc or about 690°. This angle indicates that more than a single wrap is used to produce the desired mechanical advantage.

Example 2

For a v-belt clutch having a flat coefficient of friction between the band and the drum of 0.401 (as in Example 1), and requiring a mechanical advantage of 125, and desiring a wrap angle of π (180°), equation (4) is used to compute the required angle, β, of the V-belt. For the specified conditions, a V-belt angle of 0.264 radians) (15.12°) will give the required mechanical advantage.

The following two examples describe how the clutch wear rate may be reduced by reducing the shear pressure.

Examples 3-4

Consider two clutch architectures as summarized in Table 1. The first example is a two-wrap clutch where the coefficient of friction of the 5.78 radian wrap one is μ=0.635 and the coefficient of friction of the 6.28 radian wrap two is μ=0.17. The overall mechanical advantage of this system is 114. Referring to Table 1, assuming a load end normal pressure of 600 psi in the first inch of surface at the load end, the frictional interface between wrap one and the drum surface must sustain a frictional shear force spread over a linear width of 0.475" or 328 pounds per inch width of friction surface. We compute this shear stress in the following paragraphs.

Referring to Table 1, a one-inch segment of belt at the load end of the clutch under a pressure of 600 lb/in² subtends an angle, Δθ of 0.5 radians, viz, $$\Delta\theta = 2\pi\left(\frac{\text{segment length}}{2\pi r}\right) = 2\pi\left(\frac{1}{2 \cdot \pi \cdot 2}\right) = 0.5 \text{ radians}$$

The mechanical advantage obtained from that one inch segment of the belt is given by $$MA(\text{segment}) = e^{\mu \cdot \Delta\theta} = e^{(0.635 \cdot 0.5)} = 1.3737$$

From the normal load pressure of 600 psi, the load force can be calculated by $$F_{load} = P_{normal} \cdot r \cdot w = 600 \cdot 2 \cdot 0.475 = 570 \text{ lb}$$

At a point one inch from the end, the force is calculated by $$F_{1'' \text{ from end}} = \frac{F_{load}}{MA(\text{segment})} = \frac{750 \text{ lb}}{1.3737} 415 \text{ lb}$$

The shear force on the belt within the one inch segment is therefore simply $$F_{shear} = F_{end} - F_{1'' \text{ from end}} = 155 \text{ lb}$$

Resulting in a shear stress, τ, of $$\tau = \frac{F_{shear}}{\text{length} \cdot \text{width}} = \frac{155}{1'' \cdot 0.475''} = 326 \frac{\text{lb}}{\text{in}^2}$$

Such a shear stress, in that one inch, subjects the belt to considerable wear. On the other hand, the corresponding shear stress, computed for Architecture two is about 97, which value indicates that considerably less wear would result. As shown in Table 1, for wrap two, having a much smaller belt width of 0.25", and coefficients of friction of 0.17 and 0.597 for Architectures one and two respectively, the values of the shear stresses are essentially reversed, relative to those obtained for wrap one.

TABLE 1

| Clutch Parameter | Architecture One | Architecture Two |
|---|---|---|
| Drum radius (in.) | 2 | 2 |
| Width of wrap one (in.) | 0.475 | 0.475 |
| Width of wrap two (in.) | 0.25 | 0.25 |
| Coefficient of friction $\mu_1$ of wrap one | 0.635 | 0.17 |
| Coefficient of friction $\mu_2$ of wrap two | 0.17 | 0.597 |
| Wrap angle (radians) for wrap one | 5.78 | 5.78 |
| Wrap angle (radians) for wrap two | 6.28 (2π) | 6.28 (2π) |
| Mechanical advantage for wrap one (=exp(μ5.78)) | 39.26 | 2.67 |
| Mechanical advantage for wrap two (=exp(μ6.28)) | 2.91 | 42.49 |
| Overall Mechanical Advantage (wrap one * wrap two) | 114 | 113.4 |
| Normal pressure, $P_{normal}$, at head end (psi) | 600 | 600 |
| Load force, wrap one, ($P_{normal}$ * radius * width), lb. | 570 | 570 |
| Load force, wrap one, 1" from end, lb | 415 | 524 |
| Shear force, wrap one, lb | 155 | 46 |
| Shear stress, wrap one (Force/(width * length)). psi | 326 | 97 |
| Load force, wrap two, ($P_{normal}$ * radius * width), lb. | 300 | 300 |

TABLE 1-continued

| Clutch Parameter | Architecture One | Architecture Two |
| --- | --- | --- |
| Load force, wrap two, 1" from end, lb | 276 | 223 |
| Shear force, wrap two, lb | 24 | 77 |
| Shear stress, wrap two (Force/(width * length)), psi | 98 | 310 |

Thus, because decreasing the shear pressure tends to decrease the wear rate, the coefficient of friction should be smaller at the load end and increase towards the hold end.

Although the present invention has been shown and described with reference to particular examples, various changes and modifications which are obvious to persons skilled in the art to which the invention pertains are deemed to lie within the spirit, scope and contemplation of the subject matter set forth in the appended claims.

What is claimed is:

1. A clutch comprising:
   a. a drum having an axis, a radius, a drum-side friction surface, and a first cross section bounded by the drum-side friction surface;
   b. an open-ended belt, having an end coupled to at least one source of torque, a free end, a length, a width, a belt-side friction surface, and a second cross section bounded by the belt-side friction surface, configured to form a wrap partially, fully or a plurality of times around the drum; and
   c. an externally controllable actuator, configured to apply a force to the free end of the open ended belt, whereby the belt-side friction surface engages frictionally with the drum-side friction surface,
   wherein the first cross section and the second cross section are configured generally to mate with each other, resulting in an effective coefficient of friction between the belt-side friction surface and the drum-side friction surface that
   d. varies along the length of the belt by varying the friction materials used for frictional engagement; or
   e. varies along the width of the belt by varying the geometry of the frictional engagement along with width of the belt.

2. The clutch of claim 1, further comprising a spring for holding the belt-side friction surface generally out of contact with the drum-side friction surface.

3. The clutch of claim 2, wherein the spring is integrated with the open ended belt.

4. The clutch of claim 1, wherein the cross section of the drum comprises one or more open polygons having 3 to 20 sides.

5. The clutch of claim 1, wherein the cross section of the drum further comprises a flat portion, generally perpendicular to the radius of the drum.

6. The Clutch of claim 1, wherein the belt comprises at least one unitary or segmented protrusion, generally along the length of the belt, said at least one unitary or segmented protrusion having a generally polygonal cross section of 3 to 20 sides.

7. The clutch of claim 1, wherein the wrap is chosen from a compression wrap or a tension wrap.

8. The clutch of claim 1 wherein
   a. the belt comprises at least one protrusion along the length of the belt of generally quadrilateral cross section, said protrusion having a bottom side, and
   b. the drum comprises an open triangle or open quadrilateral shaped cross section, generally configured to mate with the at least one protrusion.

9. The clutch of claim 8, wherein the at least one protrusion on the belt has a groove in the bottom side, said groove running generally parallel to the length of the belt, wherein said groove is configured to hold a spring for holding the belt-side friction surface generally out of contact with the drum-side friction surface.

10. The clutch of claim 1, wherein the cross section of the belt comprises a generally triangular or quadrilateral shape.

11. The clutch of claim 1, wherein the second cross section has a generally triangular or quadrilateral shape and the belt has a groove along the length of the belt, wherein said groove is configured to hold a spring for holding the belt-side friction surface generally out of contact with the drum-side friction surface.

12. The Clutch of claim 1, wherein the cross section of the belt comprises a curved surface.

13. A clutch comprising:
   a. a drum having a radius, m outer engagement regions, and n inner engagement regions, wherein each of the m outer engagement regions and each of the n inner engagement regions has a drum-side cross section bounded by a drum-side friction surface, and wherein m and n may be the same or different and m=0 to 6, and n=0 to 6, subject to the condition that m+n=1 to 12;
   b. p open-ended belts, each open ended belt configured to form a wrap partially, fully or a plurality of times around its corresponding outer engagement region or its corresponding inner engagement region, wherein each of the p open ended belts has an end coupled to a source of torque, a free end, a length, and a belt-side cross section bounded by a belt-side friction surface, and wherein the belt-side cross section of each of the one or more open ended belts is configured generally to mate with the drum-side cross section of its corresponding inner or outer engagement region; and wherein p=1 to m+n;
   c. means for applying a force to each open-ended belt, whereby said each open ended belt is engaged frictionally with its corresponding inner or outer engagement region;
   wherein each drum-side cross section and its corresponding belt-side cross section are configured generally to mate with each other, resulting in an effective coefficient of friction between the belt-side friction surface and the drum-side friction surface that
   d. varies along the length of the belt by varying the friction materials used for frictional engagement; or
   e. varies along the width of the belt by varying the geometry of the frictional engagement along the width of the belt.

14. The clutch of claim 13, further comprising means for holding each one or more of the p open ended belts out of frictional contact with its corresponding inner or outer engagement region.

15. The clutch of claim 13, wherein one or more of the cross sections of the m outer engagement regions and n inner engagement regions comprises an open polygon having 3 to 20 sides.

16. The clutch of claim 13, wherein one or more of the cross sections of the m outer engagement regions and n inner engagement regions comprises a flat portion, generally perpendicular to the radius of the drum.

17. The clutch of claim 13, wherein the cross sections of one or more of the p belts comprise a generally triangular or quadrilateral shape.

18. The clutch of claim 13, wherein at least one of the p open ended-belts comprises a unitary or segmented protrusion, generally along the length of the belt, wherein the unitary or segmented protrusion has a generally polygonal cross section of 3 to 20 sides.

19. The clutch of claim 13 wherein the wrap is chosen from a compression wrap or a tension wrap.

* * * * *